United States Patent
Belew

(10) Patent No.: US 7,351,801 B2
(45) Date of Patent: Apr. 1, 2008

(54) METHOD, USE AND KIT FOR SEPARATING ALBUMIN FROM CONTAMINANTS IN A LIQUID

(75) Inventor: Makonnen Belew, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 18 days.

(21) Appl. No.: 10/514,544

(22) PCT Filed: May 15, 2003

(86) PCT No.: PCT/SE03/00792

§ 371 (c)(1),
(2), (4) Date: Nov. 12, 2004

(87) PCT Pub. No.: WO03/097693

PCT Pub. Date: Nov. 27, 2003

(65) Prior Publication Data

US 2005/0215765 A1    Sep. 29, 2005

(30) Foreign Application Priority Data

May 15, 2002   (SE) .................................. 0201518

(51) Int. Cl.
C07K 16/06   (2006.01)
C07K 17/00   (2006.01)
(52) U.S. Cl. ..................... 530/364; 530/413
(58) Field of Classification Search ................ 530/412
See application file for complete search history.

(56) References Cited

U.S. PATENT DOCUMENTS 4,093,612 A    6/1978  Travis et al.
4,308,254 A   12/1981  Tayot et al.
5,710,253 A    1/1998  Ohtani et al.
5,849,874 A * 12/1998  van der Laken et al. ... 530/364
6,617,133 B1 * 9/2003  Noda et al. ................. 435/69.6

FOREIGN PATENT DOCUMENTS

EP           0 699 687      3/1996
WO        WO 02/05959      1/2002

OTHER PUBLICATIONS

Sumi et al. Bioseparation 8: 195-200 (1999). "Purification of Recombinant Human Serum Albumin Efficient purification using STREAMLINE".*
GE Healthcare Instructions 71-5009-64 AC Ion exchange media (DEAE Sepharose Fast Flow), 2005.*
Wikipedia web site for Agarose definition, accessed on Internet at noon on Feb. 13, 2006.*
Quirk et al., "Production of recombinant human serum albumin from *Saccharomyces cerevisiae*", Biotechnol. Appl. Biochem. 11: 273-287 (1989).*

* cited by examiner

Primary Examiner—Robert Mondesi
Assistant Examiner—Arrand Desai
(74) Attorney, Agent, or Firm—Yonggang Ji

(57) ABSTRACT

The present invention is a method of separating recombinant human serum albumin (rHSA) from low molecular weight contaminants in a liquid, which method comprises the steps of: (a) providing a separation medium, which includes anion-exchanging ligands coupled to a base matrix; and (b) contacting the liquid with the separation medium to adsorb the rHSA to the ligands. In one embodiment, the functional groups of the ligands are weak anion-exchanging groups, preferably secondary amines, and the density of ligands on the base matrix is relatively high.

7 Claims, 3 Drawing Sheets

A: Native PAGE/Silver; B: SDS PAGE/Silver; C: SDS PAGE/Coomassie BB

METHOD, USE AND KIT FOR SEPARATING ALBUMIN FROM CONTAMINANTS IN A LIQUID

CROSS REFERENCE TO RELATED APPLICATIONS

This application is a filing under 35 U.S.C. § 371 and claims priority to international patent application No. PCT/SE03/00792 filed May 15, 2003, published on Nov. 27, 2003 as WO 03/097693 and also claims priority to patent application No. 0201518-8 filed in Sweden on May 15, 2002; the disclosures of which are incorporated herein by reference in their entireties.

TECHNICAL FIELD

The present invention relates to the preparation of recombinant human serum albumin (rHSA), and more specifically to a method of purification of rHSA from certain contaminants in the culture broth.

BACKGOUND

Human serum albumin (HSA) is the most abundant protein present in blood plasma, where its role is to contribute to the maintenance of osmotic pressure and to bind nutrients and metabolites, to thereby enable transport thereof. There is a large pharmaceutical and scientific interest in HSA, e.g. as a drug for treating hypoalbuminemia caused by a loss of albumin or a reduction in albumin synthesis, in hemorrhagic shock etc. In the earliest methods available, the HSA was purified from blood. However, such methods involved certain problems, for example a sporadic supply of blood, economical disadvantages and contamination with undesirable substances such as hepatitis virus and not least AIDS virus. To avoid these problems, alternative methods based on recombinant DNA techniques have more recently been developed to produce recombinant HSA (rHSA). A number of such recombinant methods have been suggested, and it has been shown that the purification of the rHSA from the fermentation broth is a crucial step for the success of the process.

For example, EP 0 612 761 (The Green Cross Corporation) discloses a method of producing recombinant human serum albumin, which is presented as being of a high purity and free of non-antigenic contaminants. The method utilises hydrophobic interaction chromatography (HIC) under specified conditions combined with other steps such as ion exchange chromatography (IEC), treatment with boric acid or a salt thereof followed by ultrafiltration, and heat treatment. As regards the ion-exchange step, anion-exchange is suggested at a pH and salt concentration where the human serum albumin is recovered from non-adsorbed fractions. The purification scheme suggested may contain one step of decolouration of HSA, which is preferably a final step. Such decolouration is performed by contacting the HSA with a chelate resin that exhibits a therein specified ligand moiety, as illustrated by N-methylglucamine groups.

Further, EP 0 570 916 (Mitsubishi Pharma Corporation) discloses an alternative process for producing recombinant human serum albumin by gene manipulation techniques, wherein the purification is by a combination of steps. More specifically, a culture supernatant is subjected to ultrafiltration, heat treatment, acid treatment and another ultrafiltration, followed by subsequent treatments with a cation-exchanger, a hydrophobic chromatography medium and an anion-exchanger. The anion-exchanger treatment used is illustrated by DEAE-Sepharosm™ employed under conditions where the HSA is not adsorbed but passed through the column. After the anion-exchanger treatment or salting-out precipitation treatment, a step of chelate resin treatment may be included to reduce the amount of colouring components defined as producer host-related substances. Preferably, the carrier moiety of the chelate resin used in this step is of a hydrophobic nature, as exemplified e.g. by polyol groups, such as N-methylglucamine groups, imino groups, amino groups, and ethyleneimino groups. In addition, it is suggested that fatty acids and esters thereof derived from the raw materials for HSA production are also removed by the suggested chelate resin treatment.

As disclosed in U.S. Pat. No. 5,710,253 (The Green Cross Corporation), decolouration can also be achieved by treating a recombinant human serum albumin with a reducing agent during the purification process. More specifically, the reducing agent is a low molecular weight compound that contains an SH group selected from the group that consists of cysteine, cysteamine, cystamine, aminopropanethiol, methionine, ethionine and glutathione, or is sulphurous acid, hyposulphurous acid, pyrosulphurour acid, phosphorous acid, sulphurous acid, phosphorous acid, pyrosulphurous acid, sulphurous acid, pyrophosphoric acid, ascorbic acid, or a salt thereof. Amine compounds that are known to suppress coloration can be used in combination with the reducing agent. The reducing agent is added either during the initial purification step or during the subsequent high grade polishing steps.

Finally, EP 0 699 687 (The Green Cross Corporation) discloses a method of purification of recombinant human serum albumin by contact with adsorbent particles suspended in a fluidised bed. However, under the acidic conditions generally employed for such expanded bed adsorption, rHSA contained in the culture medium will be rapidly degraded by proteases, hence reducing the yield of product. To overcome the problem of degradation, it is suggested therein that the culture medium is heat treated to inactivate proteases before the contact with the fluidised bed. The eluent can subsequently be subject to ultrafiltration, HIC and anion exchange chromatography.

However, there is still a need in this field of improved methods that efficiently remove contaminating low molecular weight substances, such as rHSA degradation products and pigments, from the rHSA preparation.

SUMMARY OF THE PRESENT INVENTION

Thus, one object of the present invention is to provide a separation medium, which enables efficient purification of rHSA from low molecular weight contaminants, such as rHSA degradation products that appear in a culture broth.

A specific object of the invention is a method of purifying rHSA from low molecular weight contaminants, such as rHSA degradation products, wherein the contaminants are removed without need of additives.

Another object of the invention is to provide a method of purifying rHSA from low molecular weight contaminants, such as degradation products, which method is relatively insensitive to the presence of salt, i.e. to moderately high conductivities.

A further object of the invention is to provide a method of purifying rHSA from low molecular weight contaminants, such as low molecular weight degradation products, which method is more robust than the prior art methods.

Yet another object of the invention is to provide a chromatographic method of purifying rHSA from low molecular weight contaminants, such as degradation products, by adsorption thereof to a separation medium, which method allows the removal of low molecular weight contaminants by isocratic elution.

One or more of the above defined objects can be achieved as defined in the appended claims. Further objects and advantages of the present invention will appear from the detailed description that follows.

DETAILED DESCRIPTION OF THE INVENTION

Figure 1:
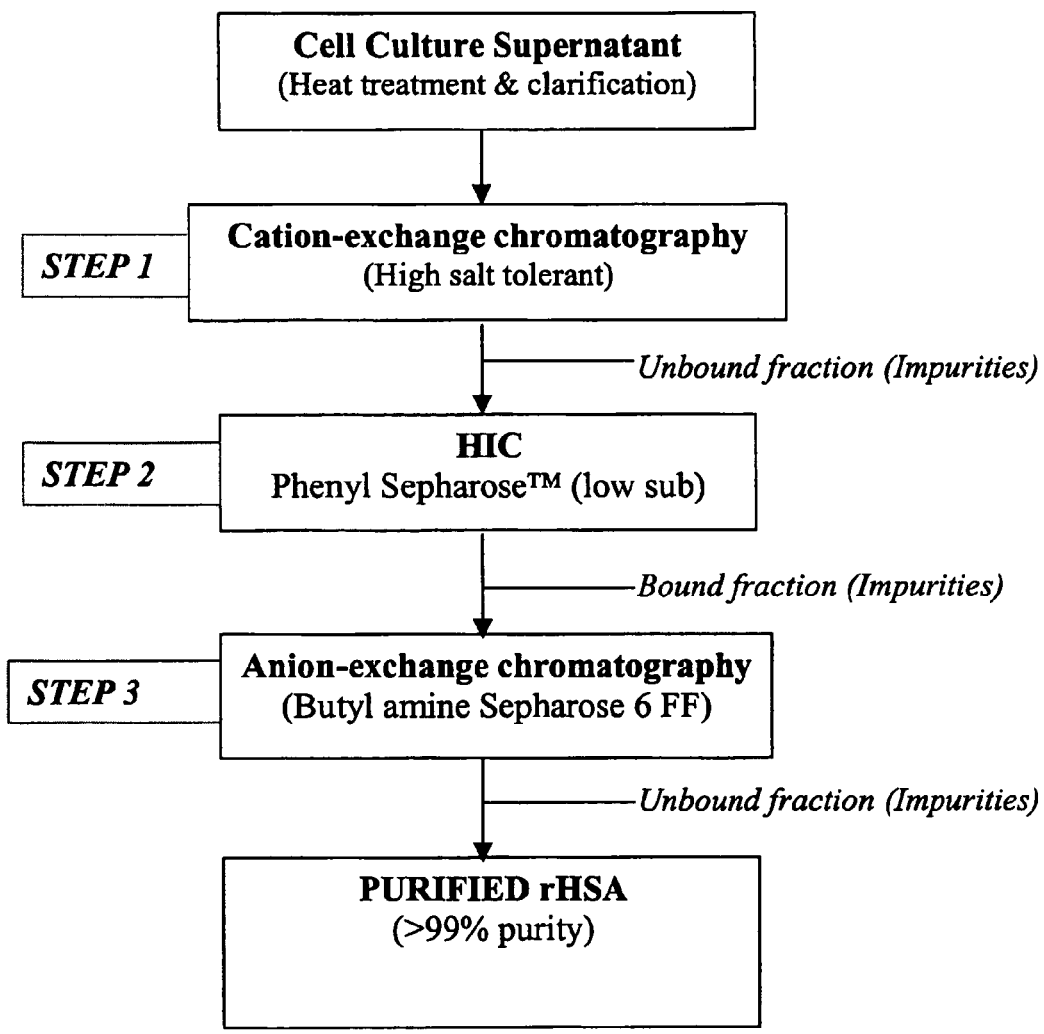
FIG. 1 shows Table 1, wherein the essentially three-step purification process that was adopted for rHSA produced by transformed yeast cells grown in a fermentation broth.

In a first aspect, the present invention relates to a method of separating recombinant human serum albumin (rHSA) from low molecular weight contaminants in a liquid, which method comprises the steps of:
(a) providing a separation medium, which is comprised of anion-exchanging ligands coupled to a base matrix; and
(b) contacting the liquid with the separation medium to adsorb the rHSA to the ligands.

Thus, in step (b), the contaminants will not be adsorbed to the separation medium. In an advantageous embodiment, the method is a chromatographic method, and accordingly the contaminants, or at least a substantial part thereof will pass through the column with the liquid. In one embodiment, the medium is washed with a suitable solution or buffer to remove non-adsorbed but retained contaminants. In the preferred embodiment, the method also comprises a subsequent step of eluting the rHSA from the separation medium by adding a solution that releases said rHSA from the ligands. Such solution, known as an eluent, is most commonly a buffer comprising a gradient of salt.

Accordingly, the present invention differs from the above-discussed prior art in the fact that the rHSA is adsorbed to an anion exchanger. Previously, anion exchangers have been utilised as one step of an rHSA purification process, but then under conditions such that the rHSA has passed the column while contaminants have been bound and/or retained. Thus, according to the present invention, it was unexpectedly found that a very efficient separation of rHSA from low molecular weight contaminants, and hence a more efficient decolouring of a sample, can be achieved by adsorbing the rHSA to the medium. In addition, the adsorbent of the present invention has also been found to be sufficiently strong to allow an efficient washing of the adsorbed rHSA, which is an advantage to obtain high yields of product. As will be discussed in more detail below, the present method is most advantageously used as a polishing step in a process of purification of rHSA.

In an advantageous embodiment, the functional groups of the ligands are weak anion-exchanging groups, preferably secondary amines. In one embodiment, the ligands are aliphatic and also comprise at least one hydroxyl group and preferably also an ether group. An example of a ligand structure that is advantageously utilised in the present method is found in the commercially available product Butyl Sepharosem™, schematically illustrated as follows:

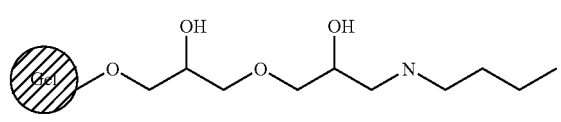

In alternative embodiments, the present invention employs an adsorbent as shown above, wherein the carbon chain to the right of the amine, i.e. on the opposite side of the amine in relation the OH groups, is comprised of a longer carbon chain. Accordingly, the adsorbent can for example end as follows: . . . N—$(CH_2)_n$, wherein n is an integer of from 1-8.

Further, it has been shown that a high density of ligands coupled to the base matrix provides advantageous results. In this context, "high" means a higher ligand density than found in the above-described Butyl Sepharose™. Accordingly, in one embodiment of the present method, the ligand density of the separation medium is at least about 50 µmol/ml medium, preferably at least about 100 µmol/ml medium and most preferably at least about 160 µmol/ml medium. As will be shown in the experimental part below, a polishing step according to the invention, using a prototype high ligand density anion exchange separation medium comprising secondary amines, has been compared with the commercially available weak anion exchange medium DEAE Sepharose™, which comprises tertiary amine groups in the form of diethylaminoethyl. It was shown that the prototype resulted in an improved decolouration and a more robust method, which is presumably due to the fact that all or substantially all of the rHSA is adsorbed i.e. bound to the prototype anion exchanger, while when DEAE Sepharose™is used, the rHSA is recovered from the unbound, but strongly retarded, fraction. Consequently, use of DEAE Sepharose™for polishing requires a more careful sample preparation procedure in order to obtain reproducible results.

Another advantage of the present invention is that it employs a non-isocratic method. Accordingly, the present method is highly repeatable. Further, the prototype weak anion exchanger which exhibits a high ligand density has been shown to be more salt tolerant than the conventional methods. Thus, it is conveniently used directly and without any substantial dilution on culture broths, wherein the salt concentration can be relatively high. Thereby, since processing volumes can be kept relatively low, substantial savings can be made, especially in large scale processing.

The base matrix to which the ligands have been coupled can be of any commonly used material, such as organic polymers, either natural or synthetic, inorganic materials, such as silica, etc. The base matrix can be in any suitable form such as particles, monoliths, surfaces, filters etc.

In one embodiment, the polymeric base matrix is comprised of a cross-linked carbohydrate material, such as agarose, agar, cellulose, dextran, chitosan, konjac, carrageenan, gellan, alginate etc. Such base matrices can easily be prepared according to standard methods, such as inverse suspension gelation (S Hjertén: Biochim Biophys Acta 79(2), 393-398 (1964). Alternatively, the base matrices are commercially available products, such as Sepharose™FF (Amersham Biosciences AB, Uppsala, Sweden). Thus, in one embodiment, the base matrix used in the present method is comprised of porous, essentially spherical polysaccharide particles, such as agarose particles.

In another embodiment, the base matrix is comprised of cross-linked synthetic polymers, such as styrene or styrene derivatives, divinylbenzene, acrylamides, acrylate esters, methacrylate esters, vinyl esters, vinyl amides etc. Such polymers are easily produced according to standard methods, see e.g. "Styrene based polymer supports developed by suspension polymerization" (R Arshady: Chimica e L'Industria 70(9), 70-75 (1988)). Alternatively, a commercially available product, such as Source™(Amersham Biosciences AB, Uppsala, Sweden) can be used according to the invention.

Coupling of anion exchanging ligands to one of the above suggested base matrices is easily performed by the skilled person in accordance with well known standard procedures, see e.g. J. Porath & T. Kristiansen in: THE PROTEINS, vol. 1, 3$^{rd.}$ edition (H. Neurath & R. L. Hill, eds) Biospecific Affinity Chromatography & Related Methods (1975) pp. 95-177.

In the present context, the term "contaminants" is used for any substance or compound that is undesired in the final rHSA preparation. As is well known, preparations of rHSA are often contaminated by certain colouring components, that are contained in the raw material or secreted by a microorganism during culture of the host microorganism, and that these contaminants bind to the rHSA to cause colouring thereof. Decolouration is also caused by degradation products of rHSA, which degradation has been caused by degrading proteases present in the culture broth. Accordingly, the method according to the invention can be defined as a process of decolouring a culture broth that comprises rHSA. Thus, in one embodiment, the low molecular weight contaminants that are separated from the product (rHSA) using the present method are rHSA degradation products. In another embodiment, the low molecular weight contaminants are of a molecular weight below 67 kDa, e.g. from 0-67 or 0-50 kDa. In one embodiment, the low molecular weight contaminants are rHSA degradation products of molecular weights in the range of about 10-46 kDa.

As appears from the above, in the most commonly used embodiment of the present method, the liquid which is applied to the separation medium is a culture broth. In the context of the present application, the term "culture broth" means the fermentation broth wherein a recombinant microorganism that produces rHSA is cultured.

As also appears from the above, production of rHSA by recombinant techniques is well known in this field, and hence the skilled person will easily be able to choose a suitable strain for expression as well as suitable conditions for culture. In brief, the host can be selected from hosts already reported in publications. Illustrative examples of the host include microbial cells, such as *Escherichia coli*, various yeast species, *Bacillus subtilis*, and animal cells, which have been made into HSA producers. Particularly preferred hosts are yeast species, especially those belonging to the genus Saccharomyces, such as *Saccharomyces cerevisiae*, the genus *Pichia*, such as *Pichia pastoris* or the genus *Kluyveromyces*, such as *Kluyveromyces lactis*. Also, auxotrophic strains or antibiotic-sensitive strains may be used.

Preparation of the HSA-producing hosts, production of HSA by culturing the hosts, and isolation and recovery of HSA from the resulting culture broth may be effected using known techniques or modified procedures thereof. For example, preparation of an HSA-producing host (or an HSA-producing strain) may be effected using a process in which a natural or modified human serum albumin gene is used. Culturing of an HSA-producing host, as well as initial isolation and recovery of HSA, may be carried out using known processes, e.g. as disclosed in the above-mentioned references. An illustrative series of steps for purification of rHSA according to the invention includes an initial capture step using a conventional cation exchanger such as SP Sepharose™ Fast Flow (Amersham Biosciences, Uppsala, Sweden), a subsequent purification step using hydrophobic interaction chromatography using e.g. Phenyl Sepharose™ 6 Fast Flow (high sub) (Amersham Biosciences, Uppsala, Sweden) followed by a polishing step using a weak anion exchanger as described by the present invention.

In a second aspect, the present invention relates to the use of an anion-exchange separation medium to reduce the amount of low molecular weight contaminants in a culture broth that comprises recombinant human serum albumin (rHSA).

In one embodiment, the anion-exchange separation medium is used to decolour a culture broth that comprises rHSA. In an advantageous embodiment, the anion-exchange separation medium comprises weak anion-exchanging groups to which the rHSA is adsorbed. In the most preferred embodiment of the present use, the ligand density of the anion-exchange separation medium is at least about 50 μmol/ml medium, preferably at least about 100 μmol/ml medium and most preferably at least about 160 μmol/ml medium. Further details regarding the present use are e.g. as described above in relation to the first aspect of the invention.

In a third aspect, the present invention relates to a kit for decolouration of a culture broth that comprises rHSA, which kit comprises an anion-exchange separation medium, which present weak anion exchanging groups coupled to a base matrix, and a solution capable of releasing the rHSA from said medium, in separate compartments as well as written instructions for the use thereof. In an advantageous embodiment, the anion-exchange separation medium is present in a chromatography column, e.g. for operations at laboratory-scale. In the most advantageous embodiment of the present kit, the ligand density of the anion-exchange separation medium is at least about 50 μmol/ml medium, preferably at least about 100 μmol/ml medium and most preferably at least about 160 μmol/ml medium. Further details regarding the anion exchange separation medium and the use are e.g. as described above.

DETAILED DESCRIPTION OF THE DRAWINGS

In FIG. 1, Table 1 is shown, which is a summary of the downstream purification process used for purifying rHSA from the cell culture supernatant of yeast cells grown in a fermentor. More specifically, Table 1 defines the steps of cation-exchange chromatography, which may be performed using high salt tolerant adsorbents, followed by hydrophobic interaction chromatography and finally the anion-exchange chromatography according to the present invention. This sequence of steps results in a purified rHSA fraction of high purity, such as above 99% purity.

Figure 2:
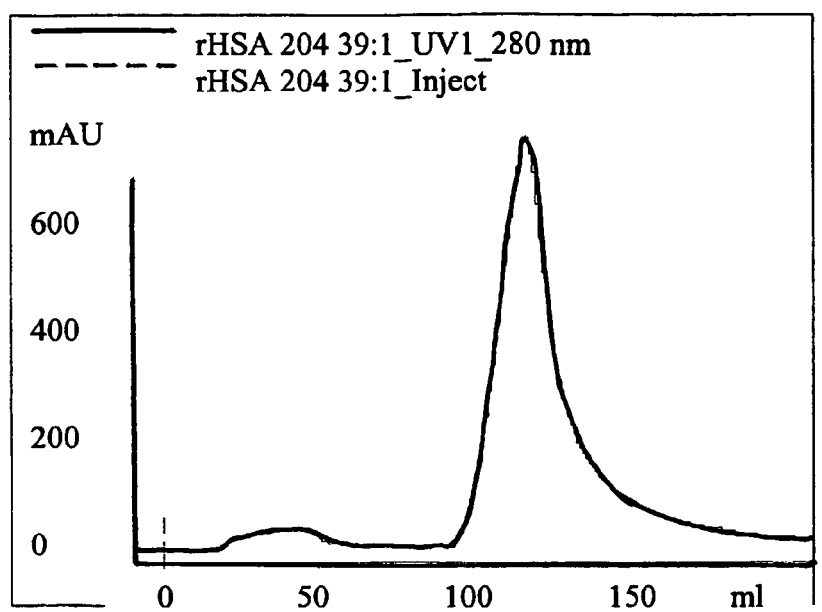
FIG. 2 shows the chromatographic elution profile obtained at the third, and final, purification step for rHSA (see Table 1). The anion-exchanger used for this final polishing step is the one that is described in the present invention. The purified rHSA is eluted in fraction 1B.

FIG. 2 shows the elution profile obtained after the third, and final, step of the chromatographic purification of rHSA (see Table 1) using a weak anion-exchanger according to the present invention. The purified rHSA is in fraction 1 B.

Figure 3:
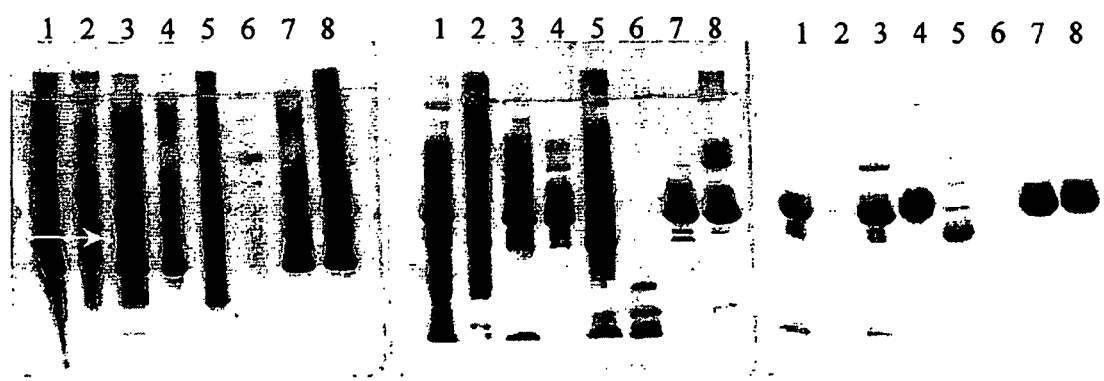
FIG. 3 shows the results of the electrophoretic analyses of the main fractions obtained using the three-step purification process shown in Table 1, wherein the last step is the polishing method according to the present invention. In the first group of eight lanes (A), Native PAGE/Silver is used; in the second group (B), SDS PAGE/Silver is used; and in the last group (C), SDS PAGE/Coomassie BB is used.

FIG. 3 shows native PAGE (8-25%) and SDS-PAGE (10-15%) analyses of the main fractions obtained during the three step purification process summarised in Table 1. The third, and last step, is the method used according to the present invention. For native PAGE analyses using the silver staining technique (FIG. 2A), about 3.3 µg of protein per spot was applied. For SDS-PAGE analyses using the silver staining technique (2B), about 2 µg of protein per spot was applied. For SDS-PAGE analyses using the Coomassie staining technique (2C), about 10 µg of protein per spot was applied.

(1): Clarified cell culture supernatant (CCS; (2): Unbound fraction from step 1; (3): Bound fraction (containing rHSA) from step 1; (4). Unbound fraction (containing rHSA) from step 2; (5): Bound fraction from step 2; (6): Unbound fraction from step 3; (7). Bound fraction (containing rHSA) from step 3; (8): Purified plasma HSA (Reference)

Figure 4:
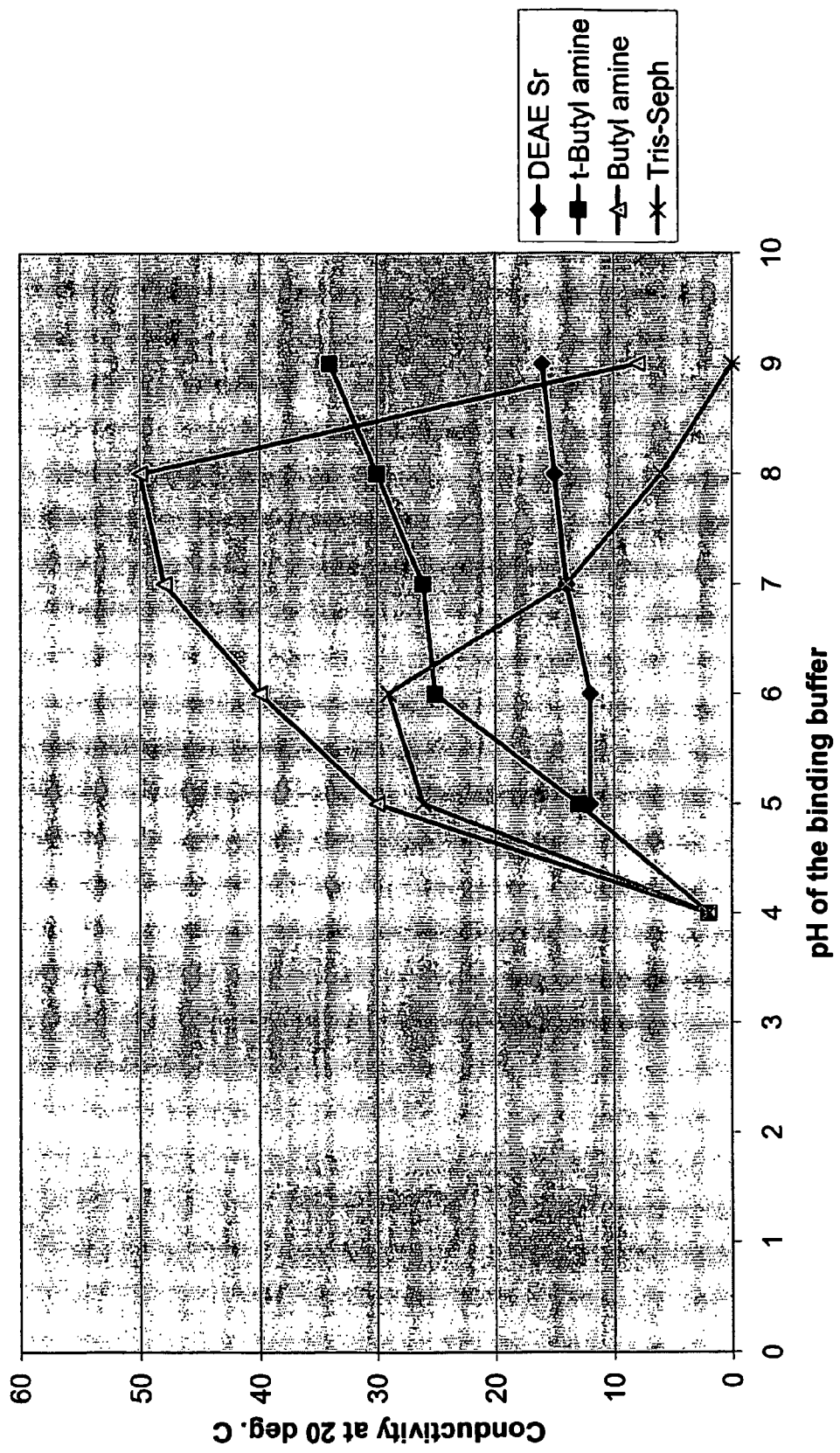
FIG. 4 shows the effect of pH on the binding of purified HSA to some commercial anion-exchangers as well as to a weak anion exchanger as used in the present invention.

FIG. 4 shows the effect of pH on the binding of purified HSA to commercial anion-exchangers as well as to a high ligand density, weak anion exchanger as used in the present invention

EXPERIMENTAL PART

The following examples are provided for illustrative purposes only, and should not be construed as limiting the invention as defined by the appended claims. All references given below and elsewhere in the present specification are hereby included herein via reference.

EXAMPLE 1

Preparation of the Weak Anion Exchanger Gel Used Below

1:1. Activation of Sepharose™ 6 FF With Allylglycidyl Ether

This is performed by reacting allylglycidyl ether with Sepharosem 6 FF under alkaline conditions.

In a suitable reaction vessel, 100 g of Sepharose™ 6 FF was mixed with 45 mL of 50% (w/w) aqueous solution of NaOH, 0.5 g of $NaBH_4$ and 13 g of $Na_2SO_4$ and. The mixture was stirred for 1 hour at 50 C. and 100 mL of allylglycidyl ether was added. The suspension was stirred for an additional 18 h at 50 deg C. The mixture was filtered and the gel washed successively with 500 mL of de-ionised water, 500 mL ethanol, 200 mL de-ionised water, 200 mL 0.2 M acetic acid, and finally with 500 mL of de-ionised water.

Analysis by titration resulted in a degree of substitution of 0.23 mmol of allyl groups/ml gel. In the following, the allyl-derivatised Sepharosem™ 6 FF will be referred to as Product I.

1:2. Activation of Product I (allylated-Sepharose™ 6 FF)

In a typical procedure, bromine water was added to a stirred suspension of 100 mL of Product I, 4 g of sodium acetate and 100 mL of de-ionised water, until a persistent yellow colour was obtained. Reduction of excess bromine was achieved by adding sodium formate to the suspension until the faint yellow colour disappeared. The reaction mixture was filtered and the allyl-derivatised gel washed with 500 mL of de-ionised water.

1:3. Coupling of N-butylamine to Activated Product I

The activated gel (Product I) was transferred to a reaction vessel followed by addition of 50 mL of N-butylamine. The suspension was stirred for 18 hours at 60 C and then filtered. The gel was washed with 500 mL of de-ionised water and its content of amine groups was determined by titration. This gave a degree of substitution of about 0.2 mmol butylamine groups/ml of gel.

EXAMPLE 2

Purification of rHSA

The example presented below will disclose a three-step purification process, wherein a cell culture supernatant (CCS), comprising rHSA, is subjected to the following chromatographic steps:
(a) cation exchange on a bi-modal, high salt-tolerant separation medium;
(b) hydrophobic interaction chromatography (HIC); and
(c) anion-exchange chromatography according to the present invention.

It is noted that the disclosures below of steps (a) and (b) are provided as illustrating one possible way of treatment of the sample before the method of the present invention as illustrated in step (c). Thus, the present invention can use as starting material any sample, preferably one that has been subjected to equivalent capture and purification steps.

Materials and Methods

The cell culture supernatant (CCS) containing rHSA was prepared by fermenting genetically-modified *P. pastoris* cells for 2 weeks or more, followed by separation of the cells by filtration. The CCS, which was green in colour, was divided into aliquots of about 200 ml and stored at −20° C. until use. The quality of the CCS was determined by gel filtration on an analytical column of Superdex™ 200 HR 10/30 (Amersham Biosciences, Uppsala, Sweden). This analysis gave the relative amounts of high molecular weight (HMW) and low molecular weight (LMW) impurities in the CCS as well as the approximate content of the monomeric form of rHSA. Sodium caprylate (octanoic acid, Na salt) and L-cysteine were bought from SIGMA Chemical Co. Chromatographically purified HSA from human plasma was kindly provided by I. Andersson at the plasma processing unit of Amersham Biosciences, Uppsala, Sweden. The concentration of protein in various samples was determined using the Bio-Rad Protein Assay kit (known as the Bradford method). Bovine serum albumin (BSA) was used to construct the standard curve. UV/Vis absorption measurements were made using a Shimadzu UV-160A recording spectrophotometer (Shimadzu Corporation, Japan). All other chemicals used were of analytical or reagent grade.

Analytical electrophoresis was performed using a PhastGel™ electrophoresis system and appropriate PhastGel™ media and buffer Strips (all from Amersham Biosciences, Uppsala, Sweden). The electrophoretic analyses were performed using native-PAGE (8-25%) or SDS-PAGE (non-reduced, 10-15%) gels according to the Manufacturer's recommendations. The amount of sample applied per spot was as follows: about 3.3 µg for native samples and 2 µg for the SDS-treated samples, both of which were stained with Silver Staining Kit (Amersham Biosciences, Uppsala, Sweden); 10 µg for the SDS-treated samples that were stained with Coomassie Brilliant Blue (CBB).

Mass spectrometric analysis (aimed at determining the mass of purified rHSA and plasma-derived HSA) were done using MALDI-TOF. Peptide mapping of the tryptic digest of the native and recombinant HSA was also done using this instrument. The results obtained from the latter analysis serve to establish the most probable primary sequence of the rHSA with reference to the known sequences of the tryptic peptides generated from purified HSA.

Matrices and Chromatography System

The chromatographic experiments were performed at room temperature (about 23° C) using an ÄKTA™ Explorer 100 system controlled by UNICORN™ (Version 3.1) software (Amersham Biosciences, Uppsala, Sweden). The separation matrix used for step (b) is Phenyl Sepharose™ 6 Fast Flow (high sub), a regular product of Amersham Biosciences, Uppsala, Sweden. For step (c), either commercially available DEAE Sepharosem™ Fast Flow (Amersham Biosciences, Uppsala, Sweden) or a modified matrix was used, i.e. Butyl Sepharose™ 6 Fast Flow (Amersham Biosciences, Uppsala, Sweden) that was produced with an increased ligand density (batch no. U238025:160 µmol/ml) as compared to the commercial product (20-40 µmol/ml gel). This modified matrix will herein be denoted "modified Butyl-Sepharose". Furthermore, step (a) utilised a prototype cation-exchanger of high salt tolerant type. This medium was packed in a XK26/20 glass column as a thick suspension in 20% ethanol to obtain a bed volume of 40 ml. A linear flow rate of 300 cm/h was used. The packed column was washed with about 2 bed volumes of de-ionised water to elute most of the ethanol and then equilibrated with the appropriate buffer solution prior to sample application.

Buffers

Buffer A: 25 mM sodium acetate, pH 4.5

Mix 25 mL of 1 M sodium acetate and 40 mL of 1 M acetic acid and dilute to 1 L with de-ionised water. Conductivity: about 2mS/cm at room temperature (RT).

Buffer B: 50 mM sodium phosphate, 0.1 M NaCl, 10 mM sodium caprylate, pH 7.0

Mix 155 mL 0.2 M $Na_2HPO_4$+95 mL of 0.2 M $NaH_2PO_4$+ 5.8 g of NaCl+1.66 g sodium caprylate and dilute to 1 L with de-ionised water. Conductivity: about 16 mS/cm at RT.

Buffer C: 50 mM sodium phosphate, 0.1 M NaCl, pH 6.0

Mix 212 mL 0.2 M $NaH_2PO_4$+38 mL of 0.2 M $Na_2HPO_4$+ 5.8 g of NaCl and dilute to 1 L with de-ionised water. Conductivity: 14 mS/cm at RT.

Buffer D: 50 mM sodium phosphate, 0.2 M NaCl, pH 6.0

Mix 212 mL 0.2 M $NaH_2PO_4$+38 mL of 0.2 M $Na_2HPO_4$ +11.7 g of NaCl and dilute to 1 L with de-ionised water. Conductivity: 22 mS/cm at RT.

Buffer E: Cleaning-in-place (CIP) solution

30% isopropanol dissolve in 1 M NaOH solution.

Heat treatment of cell culture supernatant (CCS) Before the cation-exchange chromatographic step, the CCS was heat-treated primarily to inactivate proteolytic enzymes produced during fermentation of *P. pastoris*. This was performed as follows: The frozen sample of CCS was thawed and 10 mM Na-caprylate was dissolved. The pH was adjusted to 6.0 and it was heated for 30 minutes in a water bath (maintained at 68° C. by thermostat). The sample was cooled to room temperature and its pH adjusted to 4.5.

If a conventional cation exchange medium, such as SP Sepharose™ Big Beads, was to be used for step (a), it would have been required to dilute the CCS 2-8 times, depending on the original conductivity of the solution, with de-ionised water to reach a conductivity of about 5-10 mS/cm (approximately 0.1 M salt concentration). However, the HSL-type medium used according to the present invention is much more tolerant to increased salt concentrations, and therefore the heat-treated CCS can normally be applied to step (a) without any further dilution, as long as the conductivity thereof is less than about 30 mS/cm.

The partially purified rHSA obtained after the cation-exchange step according to step (a) (i.e. the fraction bound to the HSL-type medium) was also heat-treated prior to step (b) as follows: The pH of the sample was adjusted to 6.0 with 1 M NaOH and cysteine was dissolved therein to a concentration of 5 mM to serve as a reducing agent. This solution was then heated for 60 minutes in a water bath maintained at 60° C. The main purpose of this operation is to facilitate the removal of coloured substances by the HIC medium.

EXAMPLE 2(a)

Capture Using Cation Exchange Chromatography

The cation-exchange medium was packed in an XK 16/20 column (packed bed volume 20 mL) and washed with 2 column volumes (CV) of Buffer A for equilibration. The heat-treated CCS was applied to the column via a 150 mL Superloop™ (Amersham Biosciences, Uppsala, Sweden) at a flow rate of 300 mL/h (150 cm/h). The amount of rHSA applied was about 1 g (i.e. 50 mg rHSA/ml of packed gel). After sample application, the unbound material was eluted with 3 CV of Buffer A followed by elution of the bound rHSA with 5 CV of Buffer B. The two fractions were pooled separately and the pH of the bound fraction was adjusted to 6.0 with a 1 M solution of NaOH. The solution was then heated as described above, cooled to room temperature and further purified on a HIC column as described below. A 1 mL aliquot from each pooled fraction was saved for analytical purposes (i.e. to determine protein content, the $A_{350}/A_{280}$ ratio and electrophoretic analysis).

Regeneration: The column was washed with 2 CV of Buffer E to elute very strongly bound substances and restore the function of the gel. The column was allowed to stand overnight in the same solution and then washed with 4 CV of de-ionised water to elute most of the NaOH and isopropanol. The regenerated column was re-equilibrated with 4 CV of Buffer A prior to the next cycle of adsorption/ desorption process.

EXAMPLE 2(b)

Purification Step Using HIC

The rHSA-containing fraction from the previous step was transferred to a 150 ML Superloop™ and applied to an XK26/20 column packed with Phenyl Sepharose™ Fast Flow (high sub), packed bed volume 40 mL. The column was pre-equilibrated with 3 CV of Buffer C. After sample application, the column was washed with 2 CV of Buffer C to elute the unbound material that contains the rHSA. The bound material (containing mainly the 45 kDa degraded form of rHSA) was eluted with 2 CV of de-ionised water.

Regeneration: The same procedure as above.

EXAMPLE 2(c)

Polishing According to the Invention Using a Weak Anion-Exchanger

The two fractions obtained from the previous HIC step were pooled and 1 mL aliquots from each were saved for analytical determinations (see above). A column (XK26/20) was packed with DEAE Sepharose™ Fast Flow, or the weak anion-exchanger of this invention (i.e. highly substituted Butyl Sepharose 6 Fast Flow) to obtain a packed bed volume of 40 mL. Each of the packed media was then washed with 2 CV of de-ionised water and then with about 5 CV of Buffer C to equilibrate them. The unbound fraction obtained from the HIC step was transferred to a 150 mL Superloop and applied to one or the other of the above two columns. The unbound fraction was eluted with 6 CV of Buffer C (from the DEAE Sepharose Fast Flow column) or with 2 CV from the modified Butyl-Sepharose column. The bound fraction was eluted with 2 CV of a 2 M solution of NaC 1 (for the DEAE column) or with 5 CV of Buffer D (for the column packed with the weak anion-exchanger of this invention). The flow rate was maintained at 90 cm/h throughout.

Results

The chromatographic elution profile obtained is shown in FIG. 1. Results of the PhastGel™ gradient electrophoretic analysis of the fractions obtained in this experiment (Step 3) are shown in FIG. 2. The results show that the use of the weak anion-exchanger of this invention results in the efficient removal of LMW impurities that elute as a group in the unbound fraction. Moreover, the purified fraction obtained using this IEC medium (see fraction 1 B in FIG. 1) also results in a reduced $A_{350}/A_{280}$ ratio compared with that obtained using DEAE Sepharose ™ Fast Flow medium.

Regeneration: As above.

What is claimed is:

1. A method of separating recombinant human serum albumin (rHSA) from low molecular weight rHSA degradation products in a liquid, which method comprises the step of
    (a) providing a weak anion-exchange separation medium on a base matrix suitable for separating rHSA from said low molecular weight rHSA degradation products;
    (b) contacting the liquid containing said rHSA and low molecular weight rHSA degradation products with the separation medium under conditions that allow the rHSA to adsorb and the degradation products to wash through; and
    (c) eluting said rHSA from the separation medium using a salt gradient that releases said rHSA from the ligands.

2. The method of claim 1, wherein the weak anion-exchange separation medium has ligands with the formula:

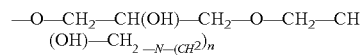

where n is an integer of 1-8.

3. The method of claim 1, wherein the weak anion-exchange separation medium has a ligand concentration of at least about 50 μmol/ml medium.

4. The method of claim 1, wherein the base matrix includes porous, essentially spherical polysaccharide particles.

5. The method of claim 1, wherein the low molecular weight degradation products are of a molecular weight below 67 kDa.

6. The method of claim 1, further comprising an additional step of washing the separation medium with a buffer between steps (b) and (c).

7. The method of claim 1, wherein the liquid is a culture broth.

* * * * *